United States Patent
Feldmann et al.

(10) Patent No.: US 7,797,055 B2
(45) Date of Patent: Sep. 14, 2010

(54) IMPLANTABLE ELECTRODE LINE

(75) Inventors: Joerg Feldmann, Berlin (DE); Jochen Palm, Mahlow (DE); Marc Schurr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 834 days.

(21) Appl. No.: 11/451,140

(22) Filed: Jun. 12, 2006

(65) Prior Publication Data

US 2007/0179578 A1 Aug. 2, 2007

(30) Foreign Application Priority Data

Jan. 31, 2006 (DE) .................. 20 2006 000 990 U

(51) Int. Cl.
*A61N 1/05* (2006.01)
(52) U.S. Cl. ............................ 607/116; 607/1; 607/2; 607/115
(58) Field of Classification Search ............... 607/1–2, 607/115–116
See application file for complete search history.

(56) References Cited

U.S. PATENT DOCUMENTS 5,344,439 A * 9/1994 Otten .................... 607/126

2003/0220677 A1 11/2003 Doan et al.

OTHER PUBLICATIONS

German Search Report for priority application, dated Sep. 20, 2006.

* cited by examiner

*Primary Examiner*—Carl H Layno
*Assistant Examiner*—Deborah Malamud
(74) *Attorney, Agent, or Firm*—ARC IP Law, PC; Joseph J. Mayo

(57) ABSTRACT

A device for stimulating a living being having proximal end having an electrical connection to an implantable medical device; having an oblong medial section having a first external diameter, which has at least one first dielectric outer envelope, at least one electrical conductor, at least one electrical stimulation and/or measurement means on the distal end; having distal section having a second outer diameter, which has at least one second dielectric outer envelope and at least one electrical conductor; having distal end having at least one electrical stimulation and/or measurement means; and having a lumen running in the longitudinal direction at least through the proximal end and the medial section. The first external diameter is isodiametric to the second external diameter, the first dielectric outer envelope has the same material properties as the second dielectric outer envelope, and the medial section has a lesser flexibility than the distal section.

16 Claims, 2 Drawing Sheets

IMPLANTABLE ELECTRODE LINE

This application takes priority from German Patent Application Serial No. 20 2006 000 990.6 filed Jan. 31, 2006 the specification of which are hereby incorporated herein by reference.

BACKGROUND OF THE INVENTION

1. Field of the Invention

The present invention relates to an implantable electrode line for electrostimulation and particularly to a device having the features claimed herein.

2. Description of the Related Art

Electrode lines of this type are used in particular in the field of cardiology and are used for transmitting pulses from implantable medical devices such as cardiac pacemakers, defibrillator/cardioverters, a combination of both, or any other device to the heart.

Such electrode lines are known from the related art and are sketched in FIG. 1. They comprise a proximal end (not shown in FIG. 1), a medial section 11, a distal section 12, and a distal end 13. The proximal end comprises a standardized plug, using which the electrical contact to an implantable medical device is produced.

The medial section 11 comprises a first dielectric outer envelope and at least one electrical conductor, which conducts the electrical pulse to the electrical stimulation and/or measurement means (110 and 130).

At least the proximal end and the medial section 11 have a lumen running in the longitudinal direction, through which a guide wire may be guided in order to be able to place the electrode line at the desired position in a blood vessel, for example.

Furthermore, stimulation and/or measurement means 110 are provided at the distal end of the medial section, which may deliver a stimulation pulse to the surrounding tissue and/or may record physiological measured values.

The distal section 12 adjoins the distal end of the medial section 11. This distal section 12 is constructed similarly to the medial section 11, namely having a second dielectric outer envelope and at least one electrical conductor for relaying an electrical pulse. The distal section does not have stimulation and/or measurement means, however. A lumen running in the longitudinal direction may also be located in this area.

The distal section 12 must have an increased flexibility, in order to be better guided through a blood vessel with its coils, for example. If there is no increased flexibility here, injuries may result during implanting of the electrode line or an electrode line may not be guided through curvy vessels—as exist in the heart area, for example.

In order to allow the flexibility, reducing the external diameter of the dielectric envelope of the distal section is known from the related art. This means the distal end having the stimulation and measurement means and the medial area project radially out of the external diameter of the distal section. The material tapering results in increased flexibility in this area. (See FIG. 1)

In the achievement of the object known from the related art, the problem is the loss of the isodiametry just described. Such an electrode line—like any other implantable device—grows into the tissue. Such undercuts grow in such a way that removal is no longer possible or is only possible with difficulty. For electrode lines, the problem additionally arises that the location at which the ingrowth occurs is not accessible.

If an electrode line is to be removed, the attempt is made to exert a tractive movement in the proximal direction from the proximal end. If the electrode has grown in at this undercut, non-isodiametric section of the distal section, in the simplest case, it may be more difficult to remove the electrode, but in the worst case this may result in injury at to the tissue or even in the distal end of the electrode line being torn off. Such injuries or tearing off such parts may result in grave, life endangering states for the patient.

BRIEF SUMMARY OF THE INVENTION

The present invention is based on the object of avoiding the disadvantages of the related art, namely providing an electrode line which is easy to implant, but which is also easy to explant again, largely without injury.

This object is achieved according to the present invention by a device having all of the features claimed herein.

The achievement of the object according to the present invention has a first external diameter in a medial section, which is isodiametric to a second external diameter, which is located in a distal section. Easy, largely injury-free explanation is thus made possible.

The electrode line according to the present invention has a distal section which has a higher flexibility than the medial section. A further advantage of the achievement of the object according to the present invention is that an increased flexibility is provided by at least partially reducing the material in the inner wall of the second dielectric outer envelope. This reduction preferably comprises annular grooves or especially preferably at least one spiral groove. The at least one spiral groove runs over the complete distal section. This has the advantage that the implantation of the electrode line is made easier and injuries are avoided. Guiding the electrode line through curvy vessels—as exist in the heart area—is made easier, for example.

A further feature according to the present invention is that the first dielectric outer envelope has the same material properties as the second dielectric outer envelope, which may also mean that the second dielectric outer envelope may preferably be made of the same material as the first dielectric outer envelope. This material is preferably silicone, especially preferably silicone having a Shore hardness of 30 A. In addition to the advantages cited, this has a positive effect during manufacturing of the electrode line.

DETAILED DESCRIPTION

Figure 1:
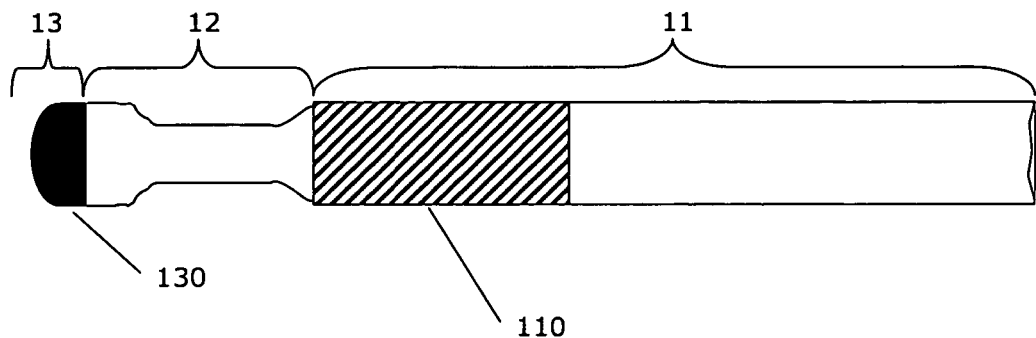
FIG. 1 shows an electrode line from the related art.
Figure 2:
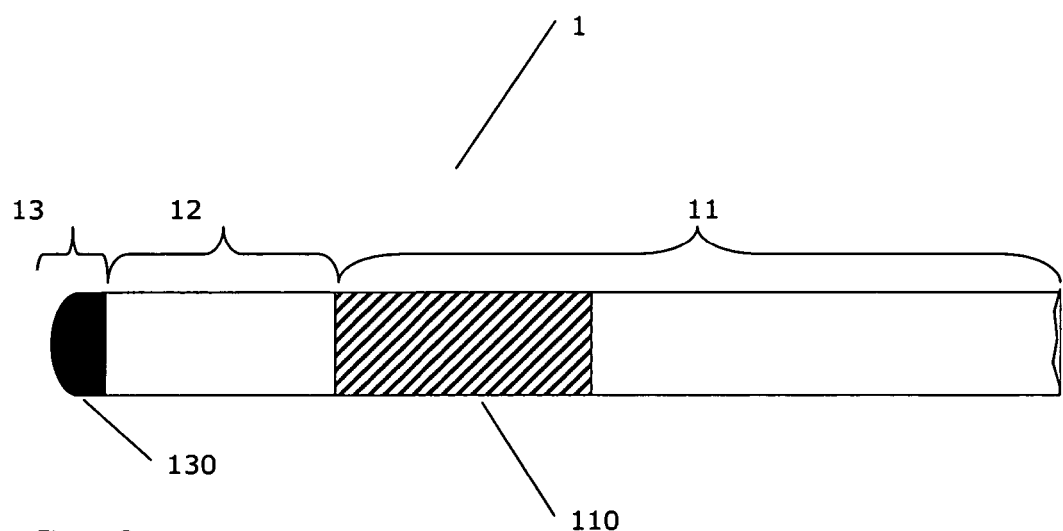
FIG. 2 shows an electrode line according to the present invention.

FIG. 2 shows the electrode line 1 according to the present invention. It comprises a proximal end (not shown), a medial section 11, a distal section 12, and a distal end 13. The second external diameter in the distal section 12 is isodiametric to the first external diameter of the medial section 11. The ingrowth of the electrode is thus reduced, which makes explanation easier.

The first and second dielectric outer envelopes are made of the same material, preferably silicone. However, they may also be made of any other suitable material which has a sufficient flexibility. A material having a Shore hardness of 30 A is especially preferred in this case.

Figure 3:
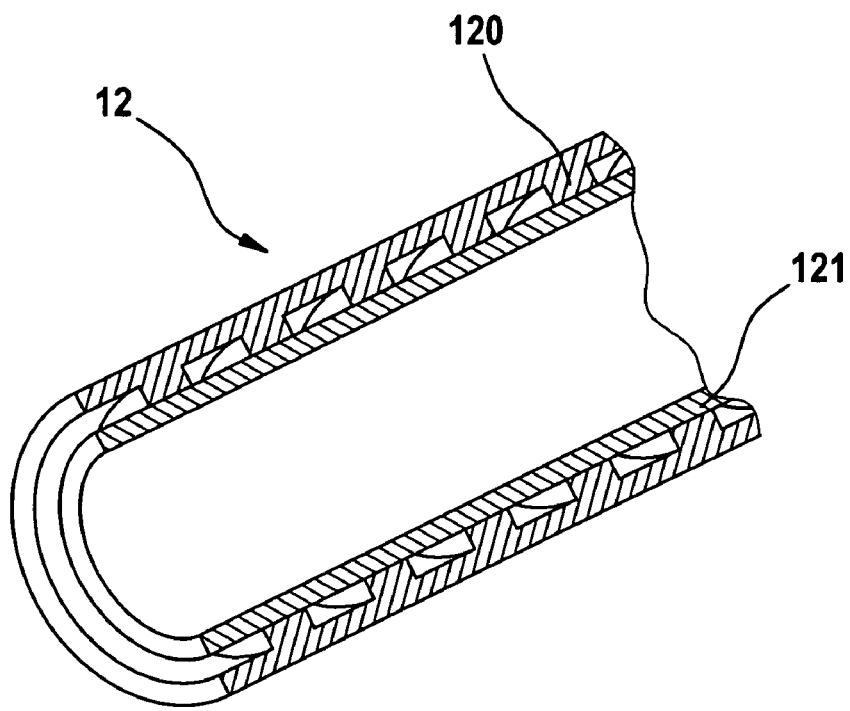
FIG. 3 shows a section through an embodiment of an electrode line according to the present invention.

FIG. 3 shows a section through the distal section 12 of the electrode line 1 according to the present invention. The dielectric outer envelope 120 and the electrical conductor 121 are shown. The electrical conductor 121 conducts impulses from and to the electrical stimulation and/or measurement means 130. A wire or, to increase the collabile strength, a wire coil, may be used as the electrical conductor. The electrical conductor 121 presses internally against the second dielectric outer envelope 120.

In order to increase the flexibility, the second dielectric outer envelope 120 has a partially reduced wall thickness. The electrical conductor 121 now thus presses only partially against the outer envelope, which results in an additional increase of the flexibility.

Figure 4:
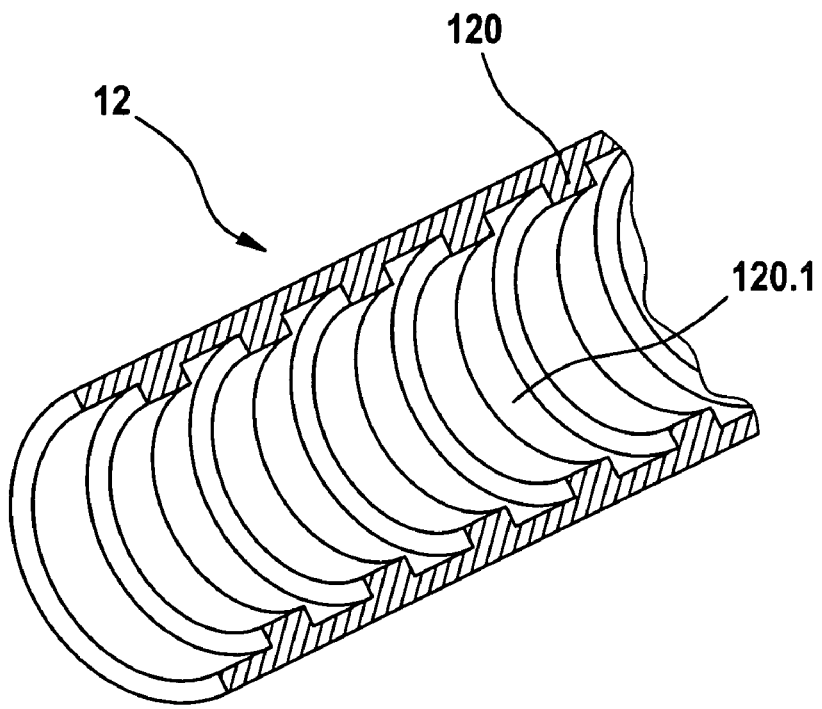
FIG. 4 shows a further section through the embodiment from FIG. 3.

One embodiment is illustrated in FIG. 4. The second dielectric outer envelope 120 is shown in the area of the distal section 12. To increase the flexibility, radial grooves 120.1 are cut or milled peripherally over the entire area of the distal section 12 in the second dielectric outer envelope 120.

In a further embodiment, at least one spiral groove, which extends over the complete second dielectric outer envelope 120, may also be milled in. If multiple spiral grooves are provided, these may have either the same slope as one another or may have different slopes. In further embodiments, the different spiral grooves may also be right and/or left-handed.

In a further embodiment, individual holes, bionic structures, or other suitable structures may also be located in the inner wall of the second dielectric outer envelope 120, which are capable of increasing the flexibility of the distal section 12.

What is claimed is:

1. A device for electrostimulation comprising:
a proximal end configured for electrical connection to an implantable medical device;
an oblong medial section having a first external diameter, wherein said oblong medial section comprises
at least one first dielectric outer envelope,
at least one first electrical conductor configured to reside within said at least one first dielectric outer envelope, and
at least one first electrical stimulation and/or measurement mechanism on a distal area of said oblong medial section wherein said at least one first electrical stimulation and/or measurement mechanism is coupled with said at least one first electrical conductor;
a distal section having a second outer diameter, wherein said distal section is coupled with said oblong medial section and wherein said distal section comprises
at least one second dielectric outer envelope, and
at least one second electrical conductor configured to reside within said at least one second dielectric outer envelope;
a distal end coupled with said distal section, wherein said distal end comprises
at least one second electrical stimulation and/or measurement mechanism wherein said at least one second electrical stimulation and/or measurement mechanism is coupled with said at least one second electrical conductor;
a lumen oriented in a longitudinal direction that passes through at least through the proximal end and said oblong medial section;
wherein said first external diameter is isodiametric to said second outer diameter;
wherein said at least one first dielectric outer envelope has the same material properties of said at least one second dielectric outer envelope; and,
wherein said distal section is configured with a greater flexibility than said oblong medial section
with said at least one second dielectric outer envelope configured with at least one indentation in an inner portion of said at least one second dielectric outer envelope to provide said greater flexibility.

2. The device according to claim 1, wherein said at least one second dielectric outer envelope has at least one section which has a lesser wall thickness than said at least one first dielectric outer envelope.

3. The device according to claim 2, wherein said at least one section of said at least one second dielectric outer envelope comprises at least one annular groove in an inner wall of said at least one second dielectric outer envelope.

4. The device according to claim 2, wherein said at least one section of said at least one second dielectric outer envelope comprises at least one spiral groove in an inner wall of said at least one second dielectric outer envelope.

5. The device according to claim 4, wherein said spiral groove runs entirely over said at least one second dielectric outer envelope.

6. The device according to claim 1 wherein said at least one first and said at least one second dielectric outer envelopes are made of silicone.

7. The device according to claim 6, wherein said silicone has a Shore hardness of 30 A.

8. The device according to claim 1, wherein said at least one second electrical conductor partially presses internally against said at least one second dielectric outer envelope to increase flexibility of said distal section.

9. A device for electrostimulation comprising:
a proximal end configured for electrical connection to an implantable medical device;
an oblong medial section having a first external diameter, wherein said oblong medial section comprises
at least one first dielectric outer envelope,
at least one first electrical conductor configured to reside within said at least one first dielectric outer envelope, and
at least one first electrical stimulation and/or measurement mechanism on a distal area of said oblong medial section wherein said at least one first electrical stimulation and/or measurement mechanism is coupled with said at least one first electrical conductor;
a distal section having a second outer diameter, wherein said distal section is coupled with said oblong medial section and wherein said distal section comprises
at least one second dielectric outer envelope, and
at least one second electrical conductor configured to reside within said at least one second dielectric outer envelope;
a distal end coupled with said distal section, wherein said distal end comprises
at least one second electrical stimulation and/or measurement mechanism wherein said at least one second electrical stimulation and/or measurement mechanism is coupled with said at least one second electrical conductor;
a lumen oriented in a longitudinal direction that passes through at least the proximal end and said oblong medial section;
wherein said first external diameter is isodiametric to said second outer diameter;

wherein said at least one first dielectric outer envelope and said at least one second dielectric outer envelope are made of a same material; and, wherein said distal section is configured with a greater flexibility than said oblong medial section with said at least one second dielectric outer envelope configured with at least one indentation in an inner portion of said at least one second dielectric outer envelope to provide said greater flexibility.

10. The device according to claim 9, wherein said at least one second dielectric outer envelope has at least one section which has a lesser wall thickness than said at least one first dielectric outer envelope.

11. The device according to claim 10, wherein said at least one section of said at least one second dielectric outer envelope comprises at least one annular groove in an inner wall of said at least one second dielectric outer envelope.

12. The device according to claim 10, wherein said at least one section of said at least one second dielectric outer envelope comprises at least one spiral groove in an inner wall of said at least one second dielectric outer envelope.

13. The device according to claim 12, wherein said spiral groove runs entirely over said at least one second dielectric outer envelope.

14. The device according to claim 9 wherein said at least one first and said at least one second dielectric outer envelopes are made of silicone.

15. The device according to claim 14, wherein said silicone has a Shore hardness of 30 A.

16. The device according to claim 15, wherein said at least one second electrical conductor partially presses internally against said at least one second dielectric outer envelope to increase flexibility of said distal section.

* * * * *